(12) United States Patent
Sulik et al.

(10) Patent No.: US 7,545,489 B2
(45) Date of Patent: Jun. 9, 2009

(54) APPARATUS AND METHOD OF INSPECTING THE SURFACE OF A WAFER

(75) Inventors: Wolfgang Sulik, Asslar (DE); Michael Heiden, Woelfersheim (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 274 days.

(21) Appl. No.: 11/463,471

(22) Filed: Aug. 9, 2006

(65) Prior Publication Data

US 2007/0052954 A1  Mar. 8, 2007

(30) Foreign Application Priority Data

Aug. 9, 2005 (DE) .................. 10 2005 038 034

(51) Int. Cl.
*G01N 21/00* (2006.01)

(52) U.S. Cl. ................. 356/237.5

(58) Field of Classification Search ............ 356/237.4, 356/237.5, 406, 414, 419
See application file for complete search history.

(56) References Cited

U.S. PATENT DOCUMENTS

| 5,822,055 | A |   | 10/1998 | Tsai et al. |
| 5,953,115 | A |   | 9/1999 | Landers et al. |
| 5,982,497 | A | * | 11/1999 | Hopkins ............... 356/419 |
| 6,570,650 | B1 | * | 5/2003 | Guan et al. ........... 356/237.4 |
| 6,700,664 | B1 | * | 3/2004 | Honda et al. .......... 356/419 |
| 6,847,443 | B1 | * | 1/2005 | Herod et al. .......... 356/237.2 |
| 6,864,971 | B2 | * | 3/2005 | Lin et al. .............. 356/237.4 |
| 6,956,644 | B2 | * | 10/2005 | Biellak et al. ......... 356/237.4 |
| 6,961,126 | B2 | * | 11/2005 | Belotserkovsky et al. ... 356/419 |
| 7,224,446 | B2 | * | 5/2007 | Kreh et al. ............ 356/237.4 |
| 7,242,478 | B1 | * | 7/2007 | Dombrowski et al. .... 356/419 |
| 7,315,377 | B2 | * | 1/2008 | Holland et al. ........ 356/419 |
| 7,345,764 | B2 | * | 3/2008 | Bulovic et al. ........ 356/419 |
| 7,403,285 | B2 | * | 7/2008 | Jung et al. ............ 356/326 |
| 2002/0107660 | A1 |  | 8/2002 | Nikoonahad et al. |
| 2002/0140930 | A1 |  | 10/2002 | Lin et al. |
| 2003/0086080 | A1 |  | 5/2003 | Guan et al. |

FOREIGN PATENT DOCUMENTS

EP   0 577 399 A2   1/1994

\* cited by examiner

*Primary Examiner*—Gregory J Toatley, Jr.
*Assistant Examiner*—Scott M Richey
(74) *Attorney, Agent, or Firm*—Darby & Darby

(57) ABSTRACT

An apparatus for inspecting a surface of a wafer includes an illumination device for illuminating an imaging area of the wafer with at least one broad-band spectrum, and an optical imaging device with a detector for polychromatic imaging of the imaging area of the wafer based on the illumination, wherein the imaging device includes a filter arrangement for selecting a plurality of narrow-band spectra. In addition, a method for inspecting the surface of a wafer, includes the steps of leveling a plurality of narrow-band spectra to a common intensity range, illuminating an imaging area of the wafer with at least one broad-band spectrum, and imaging a plurality of narrow-band spectra from the imaging area based on the illumination.

14 Claims, 2 Drawing Sheets

APPARATUS AND METHOD OF INSPECTING THE SURFACE OF A WAFER

CROSS-REFERENCE TO RELATED APPLICATIONS

Priority is claimed to German patent application DE 10 2005 038 034.4, the entire disclosure of which is hereby incorporated by reference herein.

BACKGROUND

The present invention relates to an apparatus and a method of inspecting the surface of a wafer, wherein an image of the surface of the wafer is taken for inspection which consists of a plurality of narrow-band spectra.

An apparatus and a method of the above type are known from U.S. Pat. No. 6,847,443 B1. Herein the surface of a wafer is illuminated by a light source with a plurality of narrow-band spectra, wherein the camera for imaging the surface of the wafer has sensitivity maxima corresponding to the central frequencies of the narrow-band spectra.

SUMMARY OF THE INVENTION

It is an object of the present invention to provide an optimized apparatus and method over and above the initially described state of the art.

The present invention provides an apparatus for inspecting the surface of a wafer, comprising an illumination device for illuminating an imaging area of the wafer with at least one broad-band spectrum, an optical imaging device with a detector for polychromatic imaging of the imaging area of the wafer based on the illumination, and a filter arrangement provided with the imaging device for selecting a plurality of narrow-band spectra.

The present invention also provides a method for inspecting the surface of a wafer, that includes the steps of:
  leveling a plurality of narrow-band spectra to a common intensity range;
  illuminating an imaging area of the wafer with at least one broad-band spectrum; and
  imaging a plurality of narrow-band spectra from the imaging area based on the illumination.

In a first apparatus for inspecting a wafer, comprising an illumination device for illuminating an imaging area of the wafer with at least one broad-band spectrum, and an optical imaging device having a detector for polychromatic imaging of the imaging area of the wafer based on the illumination, the imaging device includes a filter assembly for selecting a plurality of broad-band spectra. In the above arrangement an additional, fully polychromatic image of the surface of the wafer can be taken based on the illumination.

The present invention provides a second apparatus is provided for inspecting the surface of a wafer, comprising an illumination device for illuminating an imaging area of the wafer with a plurality of narrow-band spectra, and an optical imaging device having a detector for polychromatic imaging of the imaging area of the wafer based on the illumination. The illumination device or the imaging device includes a filter assembly for leveling the intensity of the spectra. Generally the plurality of narrow-band spectra have differing intensities. This can lead to overdriving of the detector for the range of the most intense spectrum. By leveling the intensities of the plurality of narrow-band spectra, overdriving of the detector is avoided for one or more of the spectra.

The present invention also provides a third apparatus for inspecting the surface of a wafer, comprising an illumination device for illuminating an imaging area of the wafer with a plurality of narrow-band spectra, and an optical imaging device having a detector for polychromatic imaging of the imaging area of the wafer based on the illumination. The illumination device and the imaging device are configured for bright-field imaging. For bright-field imaging, in particular, the illumination with a plurality of narrow-band spectra has certain advantages. In multi-layer systems with translucent layers, soft contouring by noticeable interference, i.e. deletion at the layer thickness changes, can be recognized. Due to the smaller bandwidth and therefore greater coherence of the light, the visibility of the interference effects is substantially improved on thin layers. Preferably it is also provided with the first and last mentioned apparatus, that the illumination device or the imaging device comprises a filter assembly which levels the intensity of the spectra.

Suitably it is provided that the filter assembly attenuates spectra with shorter wavelengths to a greater degree. Usually the illumination device produce the spectra having shorter wavelengths with a higher intensity. Due to the above mentioned filter assembly, the spectra are brought to the same intensity level. This is to ensure that the spectra are detected by the imaging device in a way which is uniform and free of overdriving.

Advantageously it is provided that the illumination device and the imaging device are configured for bright-field imaging. Thus the first and second apparatus can give their full benefit by combining the illumination with narrow-band spectra and bright-field imaging, as explained above.

Advantageously it is provided that the illumination device comprises three lasers. This is advantageous in that the narrow-band spectra of differing wavelengths can be provided in a cost-effective way.

It is particularly advantageous that the illumination device comprises a polychromatic light source and a filter assembly for selecting the narrow-band spectra.

The thus described embodiment of the illumination device, as against the embodiment with lasers, is advantageous in that the width of the narrow-band spectra can be determined by the filter assembly rather than being fixedly provided by the laser. This is advantageous if the narrow-band spectra are to have a minimum width in order to avoid speckles on the surface to be inspected. A continuously broad-band thermionic-emission or arc lamp can be used as the polychromatic light source, as well as a lamp having discrete spectra, such as a high-pressure mercury vapor lamp. With a lamp having discrete spectra, the filter assembly only needs to block undesirable spectral lines. This simplifies filter selection.

Ideally it is provided that the narrow-band spectra are in the visible range of the colors red, green and blue. The spectra could also be wholly or partially in the UV or IR ranges. This is advantageous in that a cheap conventional camera chip can be used as the detector. Moreover, a visible image can be created directly without resorting to false colors.

According to another embodiment of the invention it is provided that the narrow-band spectra have a spectral width of less than 20 nm, in particular less than 10 nm, in particular less than 5 nm, in particular less than 1 nm. As the band width gets smaller, the coherence of the light is increased. The visibility of interference effects on thin layers is improved. A spectral width of about 10 nm has proved to be particularly advantageous. This allows sufficient interference of the largely discrete wavelengths within the thin layer systems in question with bright-field imaging.

According to one embodiment the detector is a camera. For example, the camera can comprise an RGB CCD chip.

According to another embodiment, the detector is a three-chip camera. A three-chip camera comprises a beam splitter for splitting the light beam to be detected into three spectral ranges which are subsequently detected by three independent chips. The color splitter can split the light, for example, according to the colors red, green and blue. A three-chip camera can achieve higher resolution than a one-chip camera.

According to a preferred embodiment it is provided that the imaging device has sensitivity peaks corresponding to the spectra of the illumination device. This is advantageous in that the sensitivity of the camera matches the illuminating light provided.

The present invention also provides a method of inspecting the surface of a wafer, comprising the following steps:
  illuminating an imaging area of the wafer with at least one broad-band spectrum,
  imaging a plurality of narrow-band spectra of the imaging area based on the illumination.

The present invention also provides a second method of inspecting the surface of the wafer, comprising the following steps:
  leveling a plurality of narrow-band spectra to a common intensity range,
  illuminating an imaging area of the wafer with the leveled narrow-band spectra,
  imaging an imaging area based on the illumination.

The present invention also provides a third method including the following steps:
  illuminating an imaging area of the wafer with a plurality of narrow-band spectra at a first angle,
  imaging the imaging area based on the illumination at an angle mirrored by the wafer with respect to the first angle, so that a bright-field image is realized.

Advantageous embodiments of the above methods are analogous to the advantageous embodiments of the apparatus.

BRIEF DESCRIPTION OF THE DRAWINGS

The invention will be described in more detail in the following with reference to schematic representations of an exemplary embodiment. The same reference numerals refer to the same elements throughout the individual drawing figures, in which.

DETAILED DESCRIPTION OF THE INVENTION

Figure 1:
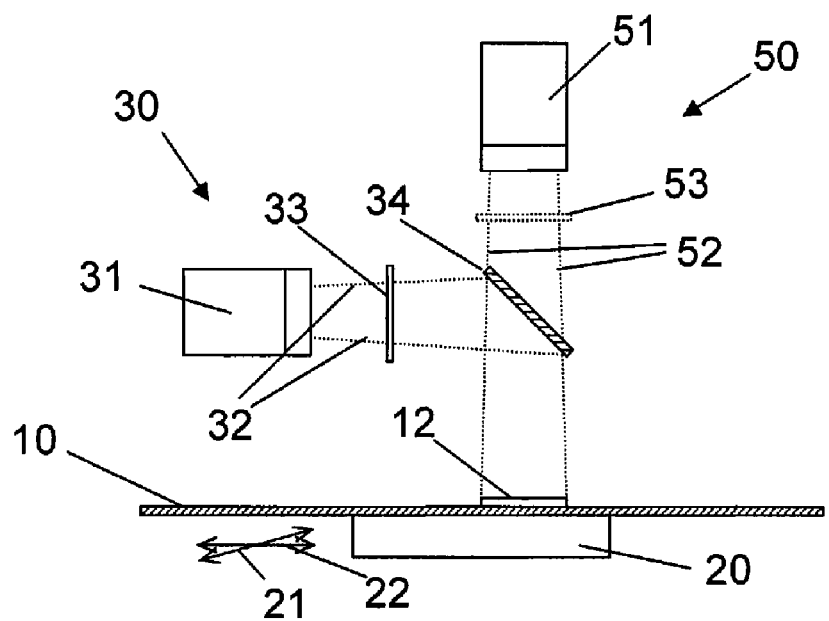
FIG. 1 is a side view of an apparatus according to the present invention.

FIG. 1 is a side view of an apparatus according to the present invention for inspecting the surface of a wafer 10. An illumination device 30 illuminates an imaging area 12 of wafer 10 which is imaged by an imaging device 50. The image imaged by imaging device 50 is processed and evaluated in an image processing unit. The image processing unit is integrated with a computer system which also controls the movement of the wafer by a transportation device 20 in directions 21 and 22 below the imaging area. Alternatively, it is also conceivable to control the illumination and imaging beams, while the wafer remains fixed. Illumination device 30 comprises a light source 31 having its illumination beam path 32 redirected by a beam splitting mirror 34 essentially vertical to the surface of wafer 10 into imaging area 12. Imaging device 50 comprises a camera 51 having a lens which images imaging area 12 of wafer 10 via its imaging beam path 52 essentially vertical to the wafer surface through the beam splitting mirror. Illumination device 30 further comprises a filter assembly 33 between light source 31 and beam splitting mirror 34.

In another alternative embodiment, instead of filter assembly 33, a filter assembly 53 can be arranged between beam splitting mirror 34 and camera 51 of imaging device 50. As a further alternative, the filter assembly can also be arranged between the beam splitting mirror and the imaging area. Combinations of these arrangements are also conceivable.

Filter 33 or its above alternative arrangements have the effect as described with reference to FIG. 3 and only transmit three narrow-band spectra in the red, green and blue ranges. Filter 33 or its alternative arrangements, for the three transmitted spectra, have a transmission decreasing from red to blue so that the red spectrum has a higher and the blue spectrum a lower transmission than the green spectrum. Instead of a filter assembly having a filter 33 in illumination device 30, as shown with respect to FIG. 4 below, a beam manipulation or unification, as shown with respect to FIGS. 4 to 6 below, can also be used. Alternatively, individual or all spectra in the UV or IR ranges are also conceivable. For all arrangements shown, the wavelengths in the range of between 365 nm (UV), 550 nm (green) and 905 nm (IR) are also conceivable. The use of 2, 4 or more narrow-band spectra is also possible.

The arrangement shown is configured for bright-field inspection with a vertical incidence of the light. Illumination device 30 illuminates the surface of wafer 10 in imaging area 12 vertically from above with three narrow-band spectra in the red, green and blue ranges. Imaging device 50 images the image formed by the light reflected in imaging area 12 through beam splitting mirror 34 vertically from above. Due to the bright-field inspection arrangement, the light incident through the illumination device on imaging area 12 interferes with transparent thin layers in the imaging area. This is how deviations in the layer thicknesses as well as deviations in the optical density can be detected due to interference effects.

Basically the arrangement can also be modified for dark-field detection.

Figure 2:
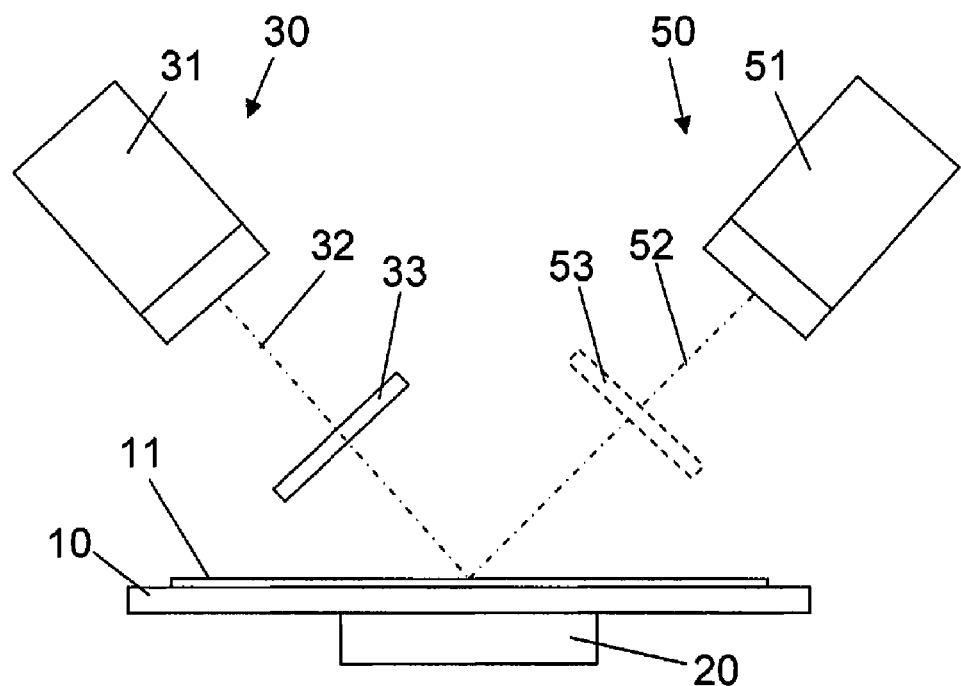
FIG. 2 is a side view of another apparatus according to the present invention.

FIG. 2 is a side view of an apparatus, according to the present invention, analogous to FIG. 1. Here, the bright-field arrangement is realized, however, with light incident at an oblique angle. Light source 31 of illumination device 30 radiates its illumination beam 32 through filter assembly 33 onto a photoresist layer 11 on wafer 10 at an angle. Camera 51 of imaging device 50 records the illumination beam reflected on a photoresist layer at the same angle.

As an alternative to the arrangement shown, filter assembly 33 can be arranged as filter assembly 53 in imaging beam 52 rather than in the illumination beam.

Figure 3:
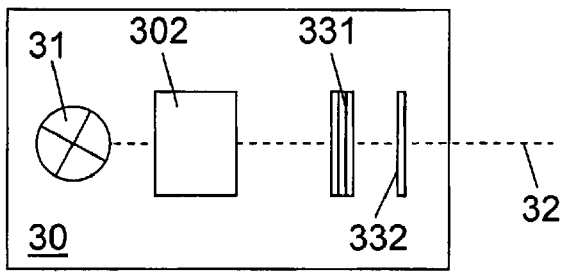
FIG. 3 shows a first illumination device with an RGB filter.

FIG. 3 shows a schematic view of the illumination device first mentioned with reference to FIG. 1 together with filter 33. Illumination device 30 comprises a light source 31, such as a white-light LED or a mercury vapor lamp. Collector 302 forms the radiation of light source 31 to an illumination beam 32 passing through RGB interference filter 331. The RGB interference filter only transmits three narrow-band spectra in the red, green and blue ranges. The adjacent absorption filter 332 attenuates the green spectrum a little and the blue spectrum a bit more. The absorption of absorption filter 332 increases continuously towards the shorter-wave end over the spectral range in question. Absorption filter 332 could also be arranged in the imaging beam or upstream of or within the arrangement for wavelength splitting.

Figure 4:
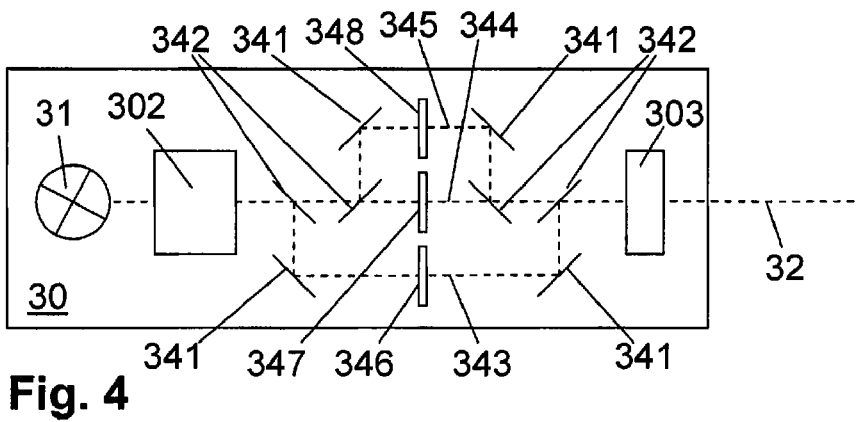
FIG. 4 shows a second illumination device with a wave-selective beam splitter.

FIG. 4 shows an illumination device 30 with a wavelength-selective beam splitting mirror. Illumination device 30 comprises a polychromatic light source 31, such as a white-light LED or a mercury vapor lamp. Collector 302 forms an illumination beam 32. Illumination beam 32 is incident on two dichroic mirrors 342, one after the other. The first beam-splitting mirror reflects red and longer-wave light, while the second beam splitting mirror blocks blue and shorter-wave light. Wavelengths in the middle, green range pass both mirrors essentially unaffected. The blue and red beams are redirected via mirrors parallel to the original illumination beam 32. Thus three parallel beams in the blue, green and red wavelength ranges are created. These three beams are passed through corresponding filters, a blue filter 348 for the blue beam, a green filter 347 for the middle, green beam and a red filter 346 for the red beam. The red, green and blue filters each only transmit a small spectrum in their red, green or blue ranges, respectively. Downstream of the red, green and blue filters are three parallel narrow-band partial beams. These partial beams are reunified via mirrors 441 and dichroic mirrors 342 to a unified illumination beam 32. A lens 303 can be inserted in the illumination beam for beam forming.

Figure 5:
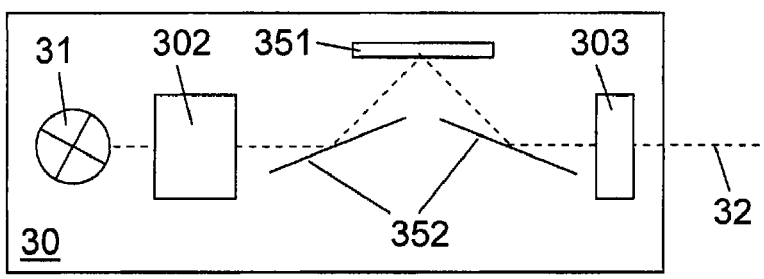
FIG. 5 shows a third illumination device with an RGB reflection filter.

FIG. 5 shows an illumination device for illuminating using a plurality of narrow-band spectra with an RGB reflection filter. Light source 31 of illumination device 30, such as a white-light LED or a mercury vapor lamp, radiates an illumination beam 32 via a collector 302 and a mirror 352 onto RGB reflection filter 351. The latter only reflects three narrow-band spectra in the red, green and blue ranges onto further mirror 352, which directs the beam into lens 303 of the imaging device. Illumination beam 32 leaves lens 303 as a beam adapted for illuminating the imaging area with three narrow-band spectra in the red, green and blue ranges.

Figure 6:
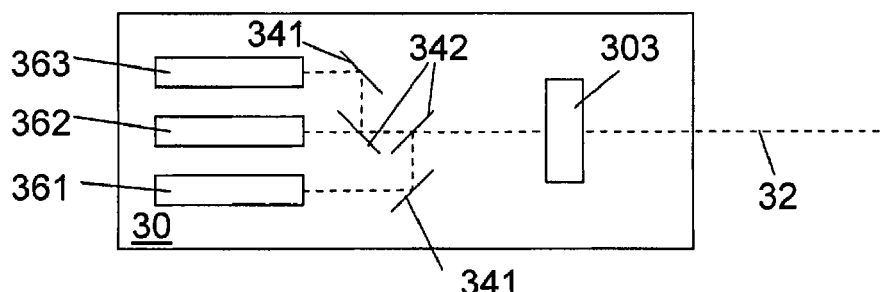
FIG. 6 shows a fourth illumination device with three laser sources.

FIG. 6 shows an illumination device 30 with three lasers. The beams of a red laser 361, a green laser 362 and a blue laser 363 are overlapped using mirrors 341 and dichroic mirrors 342 to form a unified illumination beam 32 which is passed through a lens 303 to be adapted to the imaging area. Instead of the three lasers, three LEDs of corresponding wavelengths together with collectors could also be used.

The arrangements and methods shown are mainly for the so-called macro-inspection of wafers. They are not limited to these, however.

What is claimed is:

1. An apparatus for inspecting a surface of a wafer, comprising:
    an illumination device for illuminating an imaging area of the wafer with an illumination light beam having at least one broad-band spectrum so as to form an imaging beam; and
    an optical imaging device with a detector for polychromatic imaging of the imaging beam corresponding to the imaging area of the wafer, wherein the imaging device includes a filter arrangement disposed in the imaging beam for selecting a plurality of narrow-band spectra, the narrow band spectra including spectra corresponding to the colors red, green and blue of the visible range and each having a spectral width of less than 20 nm, and the detector being a three-chip camera which has sensitivity peaks corresponding to the narrow band spectra.

2. The apparatus as recited in claim 1, wherein the illumination device has a further filter arrangement which levels an intensity of the spectra.

3. The apparatus as recited in claim 1, wherein the filter arrangement attenuates the shorter-wave spectra to a greater degree.

4. The apparatus as recited in claim 1, wherein the illumination device and the imaging device are configured for bright-field imaging.

5. The apparatus as recited in claim 1, wherein the illumination device comprises three lasers.

6. The apparatus as recited in claim 1, wherein the narrow-band spectra comprise a spectral width of less than 10 nm.

7. The apparatus as recited in claim 1, wherein the narrow-band spectra comprise a spectral width of less than 5 nm.

8. The apparatus as recited in claim 1, wherein the narrow-band spectra comprise a spectral width of less than 1 nm.

9. A method for inspecting the surface of a wafer, comprising:
    leveling a plurality of narrow-band spectra to a common intensity range;
    illuminating an imaging area of the wafer with an illumination beam of a polychromatic light source having at least one broad-band spectrum so as to form a detection beam;
    selecting a plurality of narrow-band spectra from the detection beam with a filter arrangement, the narrow band spectra including spectra corresponding to the colors red, green and blue of the visible range and each having a spectral width of less than 20 nm; and
    imaging the plurality of narrow-band spectra with a three-chip camera having sensitivity peaks corresponding to the narrow band spectra.

10. The method as recited in claim 9, wherein the illuminating includes illuminating the imaging with a plurality of narrow-band spectra at a first angle, and further comprising mirroring the imaging area based on the illumination at an angle by the wafer with respect to the first angle.

11. The method as recited in claim 9, further comprising performing an equalization step so as to attenuate shorter wavelengths to a greater degree.

12. The method as recited in claim 9, wherein the imaging is performed in a bright-field mode.

13. The method as recited in claim 9, wherein ther illumination is performed using three lasers.

14. The method as recited in claim 9 wherein during imaging, sensitivity peaks of the imaging device are overlapped with the spectra of the illumination device.

* * * * *